United States Patent [19]

Frigg

[11] Patent Number: 5,034,012
[45] Date of Patent: Jul. 23, 1991

[54] INTRAMEDULLARY NAIL WITH LOOP TIP
[75] Inventor: Robert Frigg, Wayne, Pa.
[73] Assignee: Synthes (U.S.A.), Paoli, Pa.
[21] Appl. No.: 439,706
[22] Filed: Nov. 21, 1989
[51] Int. Cl.⁵ ................... A61B 17/56; A61B 17/58
[52] U.S. Cl. ............................... 606/62; 606/64; 606/96; 606/104
[58] Field of Search ............... 606/62, 64, 67, 60, 606/72, 102, 103, 104, 96-98

[56] References Cited

U.S. PATENT DOCUMENTS

| | | | |
|---|---|---|---|
| 2,049,361 | 7/1936 | Ericsson | 606/103 |
| 3,441,017 | 4/1969 | Kaessmann | 606/64 |
| 4,409,974 | 10/1983 | Freedland | 606/72 X |
| 4,574,795 | 3/1986 | Georges | 606/64 |
| 4,705,027 | 11/1987 | Klaue | 606/64 |

FOREIGN PATENT DOCUMENTS

| | | | |
|---|---|---|---|
| 532698 | 9/1931 | Fed. Rep. of Germany | 606/103 |
| 1248228 | 8/1967 | Fed. Rep. of Germany | 606/64 |
| 1111748 | 9/1984 | U.S.S.R. | 606/62 |

Primary Examiner—Robert A. Hafer
Assistant Examiner—Kevin G. Rooney
Attorney, Agent, or Firm—Davis Hoxie Faithfull & Hapgood

[57] ABSTRACT

An intramedullary nail for use in osteosynthesis is provided with means for forming and then tightening a loop of wire extending from its distal end. In the method of its use, a locking bolt which prevents rotation and longitudinal movement of the nail is inserted through a loop more easily than through the bolt holes at the distal end of a conventional nail.

17 Claims, 4 Drawing Sheets

INTRAMEDULLARY NAIL WITH LOOP TIP

FIELD OF THE INVENTION

The invention relates to a method for treating bone fractures by means of an intramedullary nail and to an intramedullary nail for use in treatment of bone fractures.

BACKGROUND OF THE INVENTION

In conventional practice, intramedullary nails are driven down through the medulla of a fractured bone, usually one of the long bones of the leg. The nail is provided with holes through which locking bolts or retaining pins are inserted transverse to the nail and bone to secure the nail in the desired position. The locking bolts retain the nail against rotation and longitudinal movement.

In most cases after the nail is inserted into the bone, a first locking bolt is inserted through the bone and through a transverse borehole in the nail towards the distal end of the nail. One or more additional bolts are then inserted through holes near the proximal end of the nail. This procedure is difficult because the transverse locking bolts must meet their respective boreholes precisely, even though these holes are covered by bone and soft tissue. The hole at the distal end of the nail is particularly difficult to locate as it is remote from the area of the surgeon's incision. To locate the boreholes, sighting mechanisms which use X-ray imaging are employed. This technique is complicated and can lead to a high radiation dosage for the patient and possibly for the surgeon. Meanwhile, if the hole location is incorrectly identified, part of the bone is destroyed unnecessarily.

SUMMARY OF THE INVENTION

In one aspect the invention provides a method for securing an intramedullary nail in a fractured bone comprising inserting a hollow sleeve having a looped filamentary retaining element in its interior into the medulla of the bone, extending the filamentary element from the distal end of the sleeve to form a loop in the medulla outside the sleeve, inserting a locking bolt transversely through the bone and the loop and tightening the filamentary element about the bolt. Subsequently the sleeve may be replaced or reinforced by an intramedullary nail.

In another aspect the invention comprises a device for positioning an intramedullary nail comprising a sleeve adapted to be inserted into the medulla of a bone and a looped filamentary element inside said sleeve.

In another aspect the invention comprises a device as described with means for securing the ends of the looped filamentary element to the intramedullary nail.

In yet another aspect the invention comprises an intramedullary nail as described and comprising means for forming and tightening a loop of the filamentary element extending from one end of the nail.

The invention further includes assemblies comprising the sleeve and filamentary element; the sleeve, filamentary element and nail; and the nail and filamentary element.

DESCRIPTION OF THE DRAWINGS

The invention will be further described with reference to the accompanying drawings in which.

DETAILED DESCRIPTION

Figure 1:
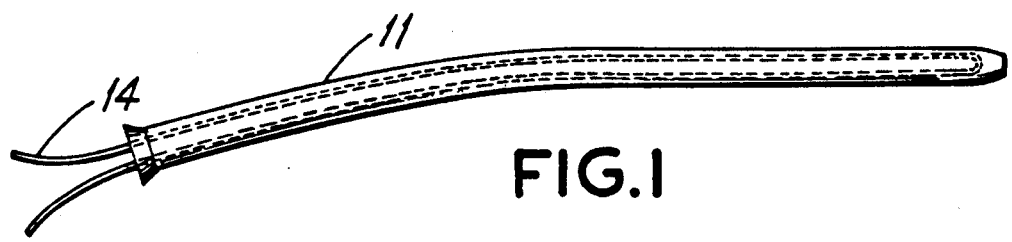
FIG. 1 is a schematic view of a device according to the invention comprising a sleeve and a looped internal filamentary retaining element.

Referring first to FIGS. 1-5, a device according to the invention in its basic form is shown in FIG. 1. As shown there it comprises a sleeve 11 and a looped filamentary element 14. The sleeve may be made out of various materials, for example physiologically acceptable metal or synthetic resin. If a synthetic resin is used it should be capable of heat sterilization. The filamentary element is preferably a metal wire or cable again made of a physiologically acceptable metal. In some instances an inert synthetic resin yarn or line may be used. Again the material should be capable of heat sterilization.

The sleeve is, of course, open at both ends and is flexible enough to follow the contours of the medulla as it is inserted.

Figure 2:
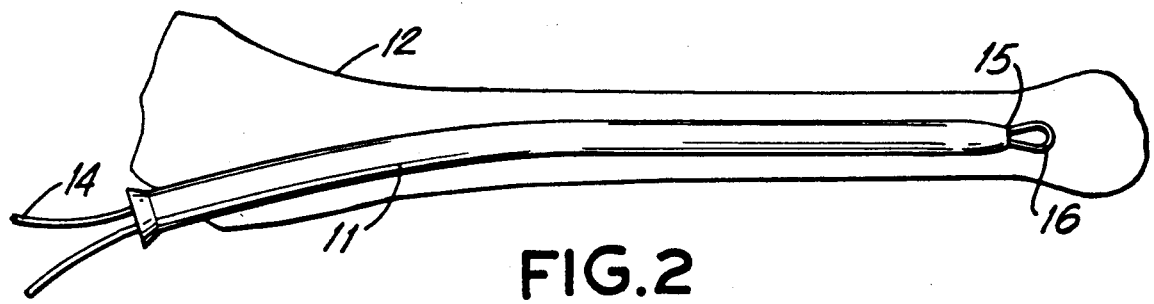
FIG. 2 is a schematic view of the sleeve of FIG. 1 inserted in a bone with the loop of the filamentary element extending from the distal end of said sleeve.
Figure 3:
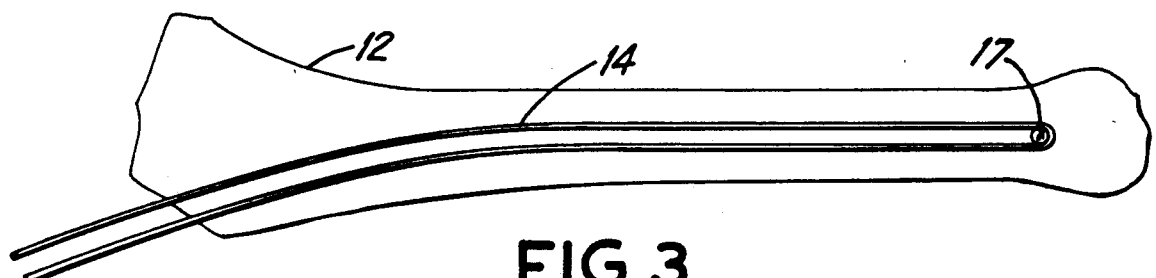
FIG. 3 is a schematic view showing a locking bolt inserted in the looped filamentary element.
Figure 4:
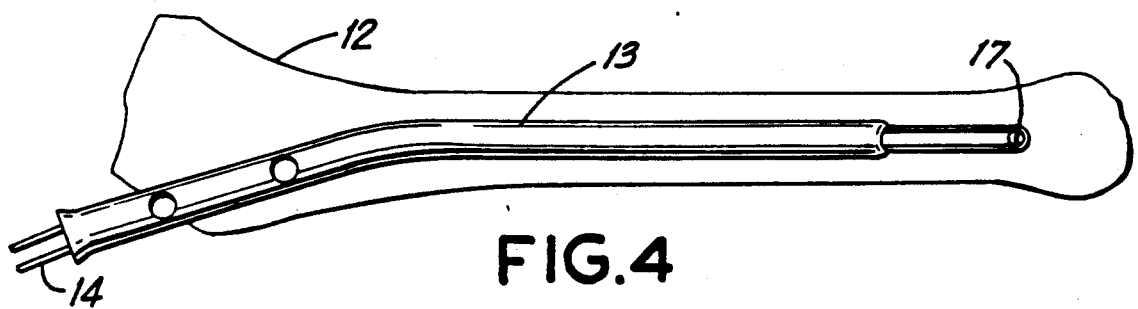
FIG. 4 is a schematic view of a device according to the invention showing a locking bolt inserted in the distal end of a bone, with a filamentary element tightly looped around it, and an intramedullary nail partially inserted into the bone around the filamentary element.
Figure 5:
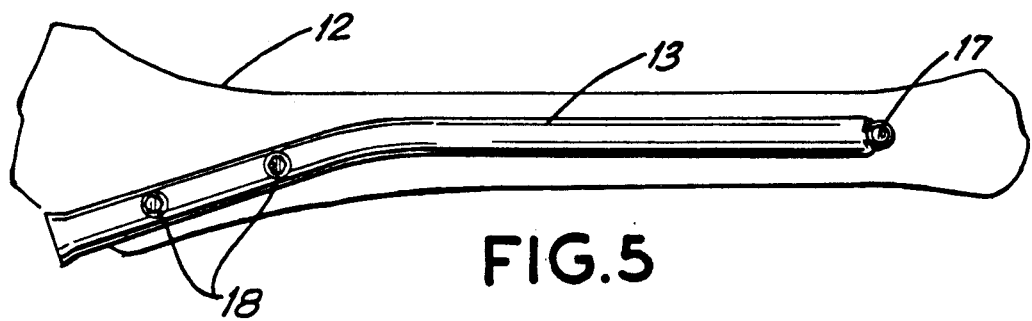
FIG. 5 is a schematic view of an intramedullary nail fully inserted and secured by locking bolts at its distal and proximal ends.
Figure 15:
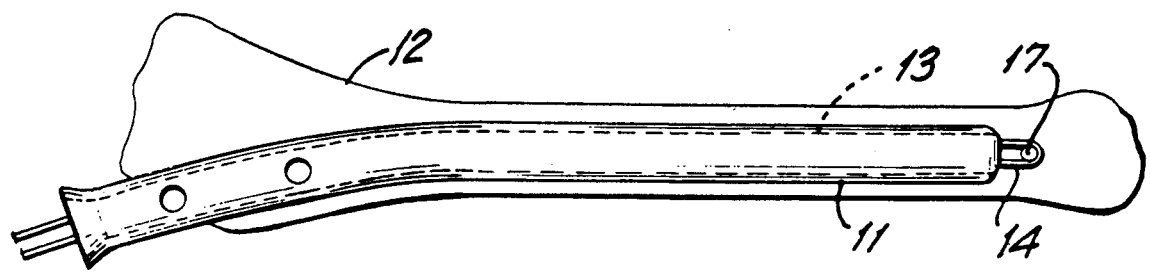
FIG. 15 is a schematic view of a device according to the invention in which a nail is inserted inside a sleeve.
Figure 16:
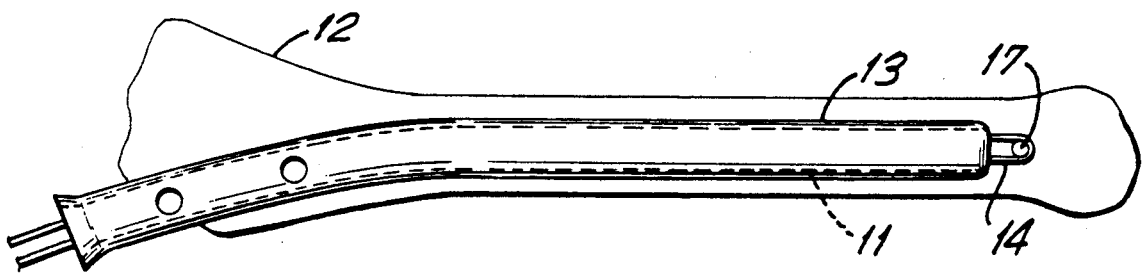
FIG. 16 is a schematic view of a device according to the invention where a nail is inserted over a sleeve.

In use, as shown in FIG. 2, sleeve 11 is inserted into the reamed-out medulla of bone 12 down to the position to which the intramedullary nail is desired to extend. As shown in FIG. 1, the element 14 is already inside the plastic sleeve 11; however it may be inserted after the sleeve 11 is in place. When the sleeve 11 is seated in the medulla, the element 14 is pushed down so that it forms loop 16 beyond the distal tip 15 of the sleeve. Within the constraints of the bore in the medulla, loop 16 may be made as large as desired, so that a transverse locking bolt or retaining pin may be inserted without fine aiming. As shown in FIG. 3, locking bolt 17 is then inserted through loop 16. After the locking bolt 17 is inserted, the element 14 is pulled tight and kept under tension. The plastic sleeve 11 may then be removed and, as shown in FIG. 4, an intramedullary nail 13 inserted into the bone 12 around filamentary element 14. Alternatively, the sleeve may be left in place and the nail inserted over or within it. The proximal end of the nail may be secured by locking bolts 18 in the conventional way and the ends of the filamentary element are secured under tension to the proximal end of the nail, preferably in the manner described below. The alternative in which the sleeve is left in place is shown in FIGS. 15 and 16. In FIG. 15, the nail 13 is inserted inside the sleeve 11. In FIG. 16, the nail 13 is inserted over the sleeve 11.

Figure 6:
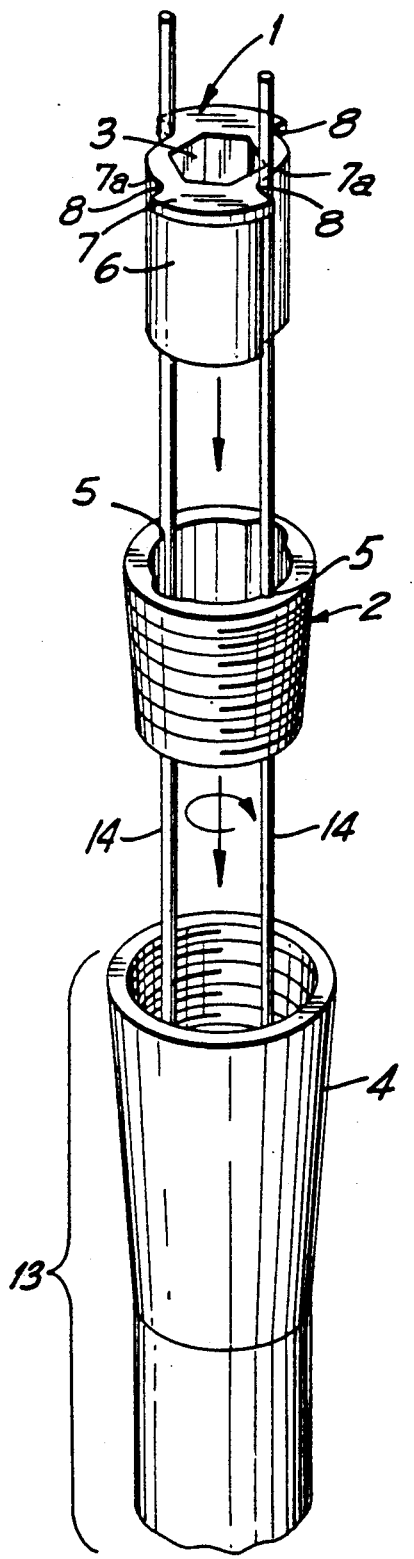
FIG. 6 is a perspective view of a section of a intramedullary nail with apparatus for locking the ends of the filamentary element.
Figure 7:
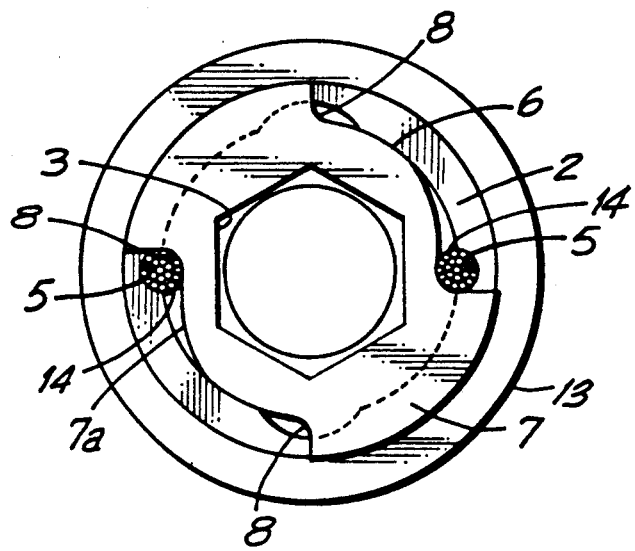
FIG. 7 is a top view of the assembled apparatus of FIG. 6, with the wire loose.
Figure 8:
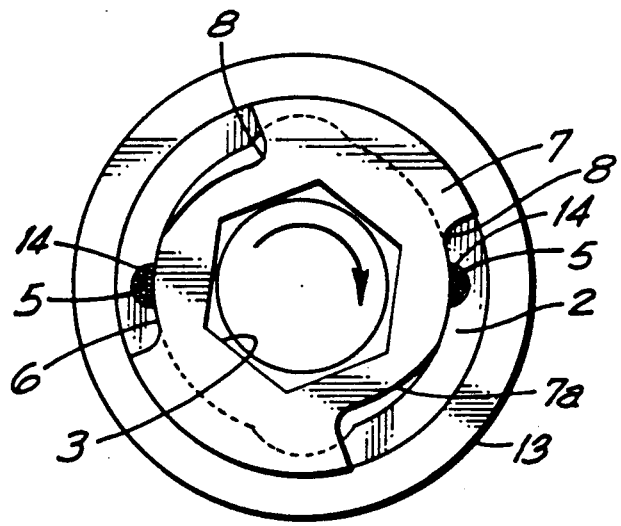
FIG. 8 is a top view of the assembled apparatus of FIG. 6, with the wire tightened.

A preferred device and method of securing the ends of the filamentary element to the nail is illustrated in FIGS. 6, 7 and 8. As shown in FIG. 6 the proximal segment 4 of nail 13 is in the shape of a truncated cone, with the proximal end wider. The inner surface of proximal segment 4 is threaded. A conical retainer 2 is provided, having its outer surface threaded to engage internal threads of the proximal segment 4 of the nail 13. The inside of retainer 2 has straight (i.e., not tapered) sides with opposing longitudinal grooves 5. Both ends of filamentary element 14 run inside retainer 2, lying in the grooves 5. A locking device 1 is provided to lock the filamentary element in the retainer 2. Locking device 1 has a stem 6 and a top 7 with curved sides 7a. Indentations 8 which can accommodate element 14 are formed in the curved sides 7a. A hexagonal longitudinal hole 3 is provided through the center of the device.

In use, retainer 2 is screwed into the socket at the proximal end 4 of nail 13, the ends of filamentary element 14 being removed from the grooves 5 as this occurs. When the retainer is fully seated, the end segments of the filament are placed in grooves 5 and locking device 1 is slid down, the sleeve 6 sliding into the central hole of the retainer with flanged upper surface 7 of locking device 1 seated on the rim of the retainer, but inside the nail 13. This arrangement is shown in FIG. 7, with the end segments of the filamentary element 14 lodged in the grooves 5 and seated in the indentations 8 of the top of the locking device 1. Using a hexagonal screwdriver the locking device is then turned clockwise. The top of the locking device then bears against the end segments of the filamentary element as shown in FIG. 8, forcing them into the grooves 5 and firmly retaining them in their desired positions in nail 13.

In the method disclosed in FIGS. 1-5, a sleeve is used to position the filamentary element in the medulla before the nail is inserted. It is, however, possible to use a nail specifically designed to be used with a filamentary retaining element and to position the filamentary element in the medulla without the use of an auxiliary sleeve. Such a device is shown in FIGS. 9-14.

Figure 9:
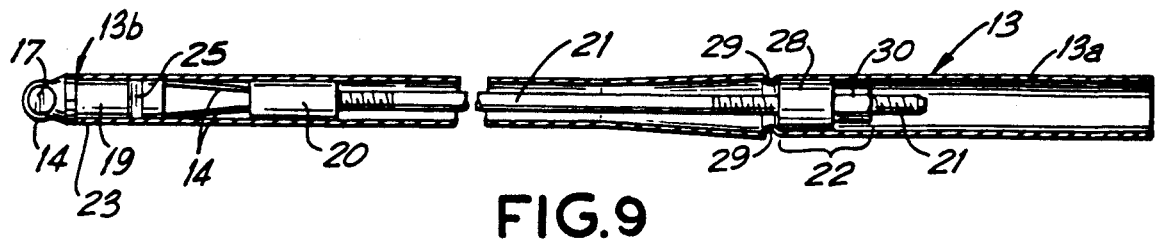
FIG. 9 is a longitudinal cross-section of an intramedullary nail according to a preferred embodiment of the invention.
Figure 10:
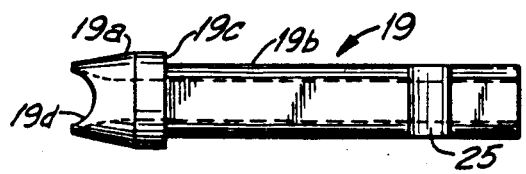
FIG. 10 is a side view of block 19 shown in FIG. 9.
Figure 11:
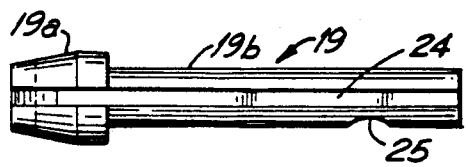
FIG. 11 is a top view of block 19.

Referring to FIG. 9 an intramedullary nail 13 has the usual elongated tubular casing 13a with an aperture 13b at its distal end. Inside the nail at its distal end is positioned a block 19, shown in detail in FIGS. 10 and 11. The block 19 has an enlarged head 19a and an extended cylindrical body 19b. The body 19b is approximately the same diameter as the internal diameter of nail 13, so that when inserted in the distal end of the nail the shoulders 19c of the head of the block abut the edge or rim of the end of the nail.

The head 19a of the block has a semi-circular cutout section 19d adapted to receive a transverse locking bolt. Grooves 24 for receiving a filamentary retaining element 14 are provided along the sides of block 19.

Figure 12:
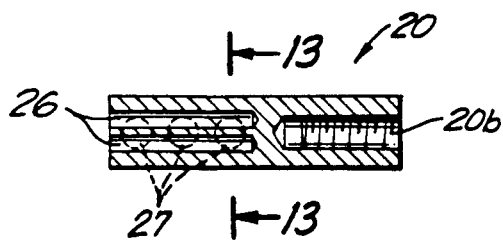
FIG. 12 is a side view in cross-section of cylinder 20 shown in FIG. 9.
Figure 13:
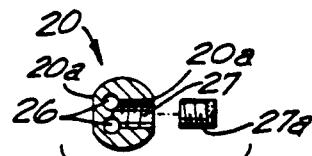
FIG. 13 is a cross-section of cylinder 20 taken at line 13—13 of FIG. 12.
Figure 14:
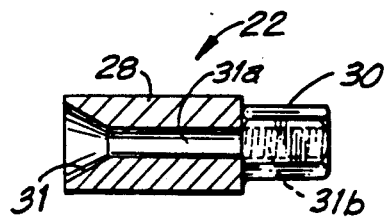
FIG. 14 is a side view in cross section of nut 22 shown in FIG. 9.

Proximal to the block 19 inside nail 13 is positioned a guide cylinder 20, shown in detail in FIGS. 12 and 13. Cylinder 20 in one transverse dimension has the same diameter as the inner diameter of the nail 13. Its sides in the transverse direction have flats 20a. Two holes 26 running parallel to the longitudinal axis of the cylinder 20 and extending about half way into the cylinder are provided for receiving the ends of the filamentary element. Transverse screw holes 27 for screws 27a are provided for retaining the ends of the filamentary element in the holes 26.

The cylinder 20 is further provided at its proximal end with a tapped socket 20b which receives the threaded end of a rod 21. Rod 21, which has a diameter smaller than the interior diameter of nail 13, extends toward the proximal end of the nail and is threaded into a nut 22 shown in detail in FIG. 14. Nut 22 has a cylindrical body 28 of a diameter approximating that of the interior of nail 13 and an extension 30 which may be given a hexagonal configuration of lesser width. The distal end of the nut has a conical entry 31, and a central passage 31a which leads to a tapped section 31b in the hexagonal extension into which rod 21 is threaded.

In use, the nail is assembled by loading the block 19, cylinder 20 and rod 21 into the nail through its distal end. The block 19 is retained in the nail by crimping the nail to engage the dimple 25 in the side of the block. The nut 22 is then slipped over the proximal end of rod 21 and engaged in the threaded extension 30, the hexagonal outer surface of the extension providing operating surfaces for a suitable socket wrench. Crimp 29 in nail 13 prevents nut 22 from moving farther distally within the nail.

Thus assembled, the nail is inserted in the medulla of the bone to be treated in the normal way. By turning hexagonal extension 30 in one direction rod 21 is moved in a distal direction, moving cylinder 20 on rod 21 and also moving filamentary element 14 distally to form a large loop at the distal end of the nail. A transverse locking bolt 17 (FIG. 9) may then be inserted through the loop of element 14. The loop is tightened about the bolt by turning the nut extension 30 in the opposite direction. This draws rod 21 in the proximal direction pulling cylinder 20 in the same direction and with it the filamentary element 14.

What is claimed is:

1. A tool useful in osteosynthesis for the insertion and positioning of an intramedullary nail comprising an elongated, tubular sleeve capable of heat sterilization and adapted for insertion into the medulla of a long bone and a looped filamentary retaining element substantially enclosed within said sleeve, said retaining element being extendable to form a loop outside one end of said sleeve.

2. A method of treating a fractured bone comprising the steps of:
   inserting a sleeve into the medulla of the fractured bone;
   placing a filamentary retaining element through the sleeve to form a loop extending from the distal end of the sleeve;
   inserting a locking bolt through the bone and through the loop; and
   inserting an intramedullary nail into the bone around the wire so that it contacts the locking bolt.

3. The method claimed in claim 2 further comprising tightening the retaining element around the bolt.

4. The method claimed in claim 2 further comprising withdrawing the sleeve before inserting the nail.

5. The method claimed in claim 2 further comprising securing the retaining element to the proximal end of the nail.

6. An assembly comprising:
a sleeve adapted to be inserted into the medulla of a bone;
a filamentary retaining element adapted to be inserted into the sleeve and to form a loop at the distal end thereof; and
a nail dimensioned to fit over the sleeve or dimensioned to fit within the sleeve.

7. A device for securing the ends of a filamentary retaining element in an intramedullary nail comprising:
a hollow retaining cylinder adapted to be inserted in one end of the nail around the ends of said retaining element; and
a locking device for insertion into said retaining cylinder thereby to pres the end segments of the filamentary retaining element against the interior of the retaining cylinder.

8. A device claimed in claim 7 wherein:
said retaining cylinder has grooves for receiving the end segments of the filamentary retaining element; and the locking device comprises a rotatable sleeve for insertion into the retaining cylinder and a top for pressing the end segments of the retaining device into the grooves, when said sleeve is rotated.

9. A device claimed in claim 8 wherein the top of the locking device has curved sides.

10. An intramedullary nail comprising a casing, a filamentary element in said casing, and means for forming a loop of said filamentary retaining element extending beyond one end of the nail.

11. An intramedullary nail having proximal and distal ends, comprising a looped filamentary retaining element for engaging a transverse locking bolt, and further comprising means for extending and withdrawing the loop of said filamentary element beyond the distal end of the nail, said last named means comprising:
a block at the distal end of the nail, said block having means for receiving said filamentary element;
a guide cylinder with means for securing the ends of the filamentary retaining element;
a rod having one end secured to said guide cylinder; and
a nut, secured to the nail adjacent its proximal end, the other end of said rod being threaded through said nut, whereby rotation of said nut moves said guide cylinder and said retaining device axially of said rod to extend or withdraw the loop of said device from the distal end of the nail.

12. A nail according to claim 11 wherein the block comprises a head adapted to engage a locking bolt.

13. A nail according to claim 11 wherein the block has transverse grooves adapted to receive the filamentary element.

14. A nail according to claim 11 wherein the block has a dimple for retaining it in the nail by crimping.

15. A nail according to claim 11 wherein the means for holding the ends of the filamentary element comprises holes extending into the guide cylinder parallel to its longitudinal axis to receive the ends of the filamentary element, and means for securing the ends of the filamentary element in said holes.

16. A nail according to claim 11 wherein the proximal end of the guide cylinder comprises a tapped socket and the distal end of the rod is threaded.

17. A nail according to claim 11 wherein said nut comprises:
a cylindrical body;
a hexagonal extension of lesser diameter than said cylindrical body; and
a conical entry at its distal end, adapted to receive the rod.

* * * * *

UNITED STATES PATENT AND TRADEMARK OFFICE
CERTIFICATE OF CORRECTION

PATENT NO. : 5,034,012

DATED : July 23, 1991

INVENTOR(S) : Robert Frigg

It is certified that error appears in the above-identified patent and that said Letters Patent is hereby corrected as shown below:

Col. 3, line 39, after "retainer" insert --2--.

Col. 5, line 22, delete "pres" and insert -- press--.

Signed and Sealed this

First Day of December, 1992

Attest:

DOUGLAS B. COMER

*Attesting Officer*   *Acting Commissioner of Patents and Trademarks*